US011116930B2

(12) United States Patent
Hart

(10) Patent No.: US 11,116,930 B2
(45) Date of Patent: Sep. 14, 2021

(54) CONTROLLING OXYGEN CONCENTRATOR TIMING CYCLE BASED ON FLOW RATE OF OXYGEN OUTPUT

(71) Applicant: Caire Inc., Ball Ground, GA (US)

(72) Inventor: Beau Hart, Ball Ground, GA (US)

(73) Assignee: CAIRE INC., Ball Ground, GA (US)

( * ) Notice: Subject to any disclaimer, the term of this patent is extended or adjusted under 35 U.S.C. 154(b) by 925 days.

(21) Appl. No.: 14/670,979

(22) Filed: Mar. 27, 2015

(65) Prior Publication Data

US 2015/0273174 A1    Oct. 1, 2015

Related U.S. Application Data

(60) Provisional application No. 61/971,632, filed on Mar. 28, 2014.

(51) Int. Cl.
*A61M 16/10* (2006.01)
*B01D 53/047* (2006.01)
(Continued)

(52) U.S. Cl.
CPC ....... *A61M 16/101* (2014.02); *B01D 53/0476* (2013.01); *A61M 16/0063* (2014.02);
(Continued)

(58) Field of Classification Search
CPC ............ A61M 16/0063; A61M 16/101; A61M 16/201; A61M 16/202; A61M 2202/0208; A61M 2205/3334; A61M 2205/3358; A61M 2205/3368; A61M 2205/50; A61M 16/00; B01D 2255/50; B01D 2256/12;
(Continued)

(56) References Cited

U.S. PATENT DOCUMENTS 4,927,434 A * 5/1990 Cordes ............... B01D 53/0454
95/15
5,099,837 A * 3/1992 Russel, Sr. ........ A61M 16/0677
128/204.26
(Continued)

FOREIGN PATENT DOCUMENTS

CN    102665812 A    9/2012
EP     2497516 A1    9/2012
(Continued)

OTHER PUBLICATIONS

Extended European Search Report, Supplementary Search Report and Search Opinion, dated Nov. 11, 2017 for Application No. 15770044.4-1664 / 3122411 PCT/US2015022970.
(Continued)

*Primary Examiner* — Jan Christopher L Merene
*Assistant Examiner* — Ned T Heffner
(74) *Attorney, Agent, or Firm* — Leason Ellis LLP

(57) ABSTRACT

A control circuit of an oxygen concentrator maintains pressure within a compressor of the oxygen concentrator. The control circuit includes a microprocessor that controls functioning of a controller based on two or more of: a user-adjustable flow rate of oxygen delivered by the oxygen concentrator to a user, an ambient temperature, and an ambient pressure. The functioning of the controller further controls the adsorption of various gases by sieve beds of the oxygen concentrator to produce oxygen enriched gas.

22 Claims, 3 Drawing Sheets

(51) Int. Cl.
    *A61M 16/00*   (2006.01)
    *A61M 16/20*   (2006.01)
(52) U.S. Cl.
    CPC ......... *A61M 16/201* (2014.02); *A61M 16/202* (2014.02); *A61M 2202/0208* (2013.01); *A61M 2205/3334* (2013.01); *A61M 2205/3358* (2013.01); *A61M 2205/3368* (2013.01); *A61M 2205/50* (2013.01); *B01D 2255/50* (2013.01); *B01D 2256/12* (2013.01); *B01D 2257/102* (2013.01); *B01D 2259/402* (2013.01); *B01D 2259/40009* (2013.01); *B01D 2259/40081* (2013.01); *B01D 2259/4533* (2013.01)
(58) Field of Classification Search
    CPC .... B01D 2257/102; B01D 2259/40009; B01D 2259/40081; B01D 2259/402; B01D 2259/4533; B01D 53/0476
    See application file for complete search history.

(56) References Cited

U.S. PATENT DOCUMENTS

| | | | | |
|---|---|---|---|---|
| 5,809,999 | A * | 9/1998 | Lang | A62B 7/14 128/200.24 |
| 5,917,134 | A | 6/1999 | Kramer | |
| 6,090,185 | A * | 7/2000 | Monereau | B01D 53/0473 95/102 |
| 6,427,690 | B1 * | 8/2002 | McCombs | A61M 16/0677 128/204.23 |
| 6,712,876 | B2 * | 3/2004 | Cao | B01D 53/047 95/10 |
| 6,764,534 | B2 * | 7/2004 | McCombs | B01D 53/0446 96/111 |
| 7,204,249 | B1 | 4/2007 | Richey, II et al. | |
| 7,445,663 | B1 * | 11/2008 | Hunter | B01D 53/047 128/204.21 |
| 2002/0127442 | A1 * | 9/2002 | Connor | B01D 53/047 429/408 |
| 2003/0167924 | A1 * | 9/2003 | McCombs | B01D 53/0446 96/121 |
| 2005/0217668 | A1 * | 10/2005 | Figley | A61M 16/0666 128/200.23 |
| 2006/0102181 | A1 * | 5/2006 | McCombs | A61M 16/10 128/204.26 |
| 2006/0266357 | A1 * | 11/2006 | McCombs | A61M 16/10 128/204.26 |
| 2007/0227360 | A1 * | 10/2007 | Atlas | A61M 16/10 96/121 |
| 2009/0044698 | A1 * | 2/2009 | Meacham | B01D 53/0407 95/21 |
| 2009/0145428 | A1 * | 6/2009 | Sward | A61M 16/10 128/202.26 |
| 2009/0211438 | A1 * | 8/2009 | Thompson | B01D 53/047 95/22 |
| 2009/0214393 | A1 * | 8/2009 | Chekal | B01D 53/047 422/120 |
| 2010/0031960 | A1 * | 2/2010 | Knight | A61M 16/10 128/204.23 |
| 2011/0247620 | A1 * | 10/2011 | Armstrong | A61M 16/10 128/204.23 |
| 2011/0247622 | A1 * | 10/2011 | Schneider | A61M 16/10 128/204.23 |
| 2012/0000462 | A1 * | 1/2012 | Edwards | A61M 16/10 128/201.21 |
| 2012/0055477 | A1 * | 3/2012 | Wilkinson | A61M 16/024 128/204.23 |
| 2012/0272966 | A1 * | 11/2012 | Ando | A61M 16/10 128/205.27 |
| 2015/0273174 | A1 | 10/2015 | Hart et al. | |

FOREIGN PATENT DOCUMENTS

| | | |
|---|---|---|
| EP | 3122411 B1 | 3/2021 |
| JP | 2004344241 A | 12/2004 |
| JP | 2008-201657 A | 9/2008 |
| JP | 2008201657 A | 9/2008 |
| JP | 2009530084 A | 8/2009 |
| JP | 2010-209036 A | 9/2010 |
| JP | 2010209036 A | 9/2010 |
| JP | 2017510408 A | 3/2021 |
| KR | 20110094649 A | 8/2011 |
| WO | WO 2011/052803 A1 | 5/2011 |
| WO | 2013038299 A1 | 3/2013 |
| WO | 2013038315 A1 | 3/2013 |
| WO | WO 2015148911 A1 | 10/2015 |

OTHER PUBLICATIONS

Second Office Action in corresponding Chinese Application No. 201580023551.2, dated Mar. 14, 2019.
Third Chinese Office Action in corresponding Chinese Application No. 201580023551.2, dated Oct. 9, 2019 (an English translation attached hereto).
Examination Report in corresponding Canadian Application No. 2,944,040, dated Mar. 26, 2021.
Office Action issued by the Japanese Patent Office for patent application No. 2017-052939, dated Jan. 29, 2019 with English summary (Corresponding foreign application) (9 pages total).
Official Action in corresponding Japanese Application No. 2017-502939, dated Oct. 13, 2020.

* cited by examiner

CONTROLLING OXYGEN CONCENTRATOR TIMING CYCLE BASED ON FLOW RATE OF OXYGEN OUTPUT

REFERENCE TO PRIORITY DOCUMENT

This application claims priority to U.S. Patent Application Ser. No. 61/971,632 entitled "Controlling Oxygen Concentrator Timing Cycle Based on Flow Rate of Oxygen Output", filed Mar. 28, 2014. The provisional application is incorporated by reference and priority to the filing date is hereby claimed.

BACKGROUND

Oxygen concentrators typically allow a user (for example, a patient) to adjust a flow rate of oxygen based on recommendation by a clinician. Mechanically, these oxygen concentrators incorporate control schemes for adjusting the flow rate of oxygen. Oxygen concentrators typically include a compressor for compressing ambient air to support production of oxygen, one or more molecular sieve beds for concentrating oxygen, and an oxygen tank for storing concentrated oxygen.

Traditional control schemes for such oxygen concentrators incorporate a high pressure in molecular sieve beds at low oxygen flow rates due to low amounts of oxygen product being output from the oxygen tank. This increases load on the compressor, thereby shortening product-limiting service life of the compressor. In addition, the traditional control schemes adjust oxygen flow rate while performing oxygen production functions according to fixed preset time cycles, which usually include a preset high-pressure cycle step and a preset low-pressure cycle step. The fixed cycle time disadvantageously reduces the purity of the delivered oxygen at low flows, by retaining argon within the produced oxygen and disadvantageously carries over nitrogen at high flows. Moreover, the fixed cycles are not optimized for all outlet gas flow rates or for any variation in ambient air conditions such as temperature, or pressure associated with altitude.

SUMMARY

A control circuit includes a microprocessor of a pressure-swing adsorption device that enriches a flow of a gas drawn from a mixture of gases; such as an oxygen concentrator. The microprocessor controls functioning of a valve controller based on two or more of: a user-adjustable flow rate of oxygen delivered by the oxygen concentrator to a user (for example, patient), an ambient temperature, and an ambient pressure. The functioning of the controller further controls the adsorption of various gases (for example, nitrogen) by sieve beds of the oxygen concentrator to produce high purity oxygen product gas.

Computer program products are also described that comprise non-transitory computer readable media storing instructions, which when executed by at least one data processors of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems.

The subject matter described herein provides many advantages. For example, the control scheme allows the timing cycle of the oxygen concentrator to be optimized for all flow-rate values throughout the flow setting range, which can be for example 0.5 liters per minute to 5 liters per minute. The optimized cycle results in the oxygen concentrator producing oxygen with higher purity than conventional concentrators for all flow-rate values, and especially for best high-flow performance, especially at the extremes of the flow setting range. The higher purity oxygen is more beneficial for patients than oxygen with lesser purity, as produced by traditional concentrators. Further, the control scheme enables low flow rates of oxygen. These low flow rates assert a low pressure load on the compressor due to fast optimized cycles, thereby increasing reliability of the compressor. As the compressor is typically one of the components of the oxygen concentrator that most frequently requires repair, the increased reliability of the compressor can provide significant cost savings as well as providing an improved functional quality of the oxygen concentrator, including under a wide range of conditions of ambient temperature and pressure.

In one aspect, there is disclosed a gas concentrator system, comprising: a gas compressor that receives and compresses ambient air to provide a supply of pressurized gas mixture; at least two gas separation sieve beds configured to adsorb at least one gas species from the pressurized gas mixture from the compressor so as to provide an enriched gas product, wherein the gas separation sieve beds cycle between periods of pressurizing and venting; first and second valves that independently regulate flow of the pressurized gas mixture to the sieve beds; a fluid line coupled to the gas separation sieve beds, the fluid line providing the enriched gas product toward an outlet; at least two sensors coupled to the fluid line, wherein the at least two sensors are at least two of: (a) a flow rate sensor that measures a flow rate of the enriched gas product through the fluid line; (b) a temperature sensor coupled to the fluid line, wherein the temperature sensor measures ambient temperature; and (c) a pressure sensor coupled to the fluid line, wherein the pressure sensor measures ambient pressure; and a controller that selectively controls the first and second valves to control either of the periods of pressurizing and venting of the sieve beds based on at least two of the measured flow rate, ambient temperature, and ambient pressure.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the various drawings indicate like elements.

DETAILED DESCRIPTION

Disclosed is a gas concentrator system that includes a controller that selectively controls at least portions of the cycling of a pressurized gas mixture through two or more sieve beds based on at least two of a measured gas flow rate, a measured ambient temperature, and a measured ambient pressure; in order to reduce or optimize the pressures and associated compressor loading, for best efficiency, cost, size, or other design parameter of interest, or a combination of these. The controller can vary cycle times and switching times between a pressurizing mode, an equalizing mode and a venting mode in order to reduce peak pressures and compressor loading. In an embodiment, the system includes two or more independent valves that control the flow of a pressurized gas mixture to the sieve beds. In this regard, the controller selectively controls the two or more valves to control either of the periods of pressurizing and venting of the sieve beds based on at least two of a measured flow rate, ambient temperature, and ambient pressure. The system further includes a gas compressor that receives and compresses ambient air to provide a supply of pressurized gas mixture to a pair of gas separation sieve beds that adsorb a gas species from the pressurized gas mixture so as to provide an enriched gas product.

The system is described herein using a non-limiting example where the enriched gas product is oxygen or nitrogen, although the enriched gas product may vary and can be any of a variety of gases. In a non-limiting example, the system is used to direct a gas, such as oxygen, to a patient for inhalation. In another non-limiting example, nitrogen is directed to a beverage delivery system. In another non-limiting example, the enriched gas product is methane and the methane is directed to a condenser.

Figure 1:
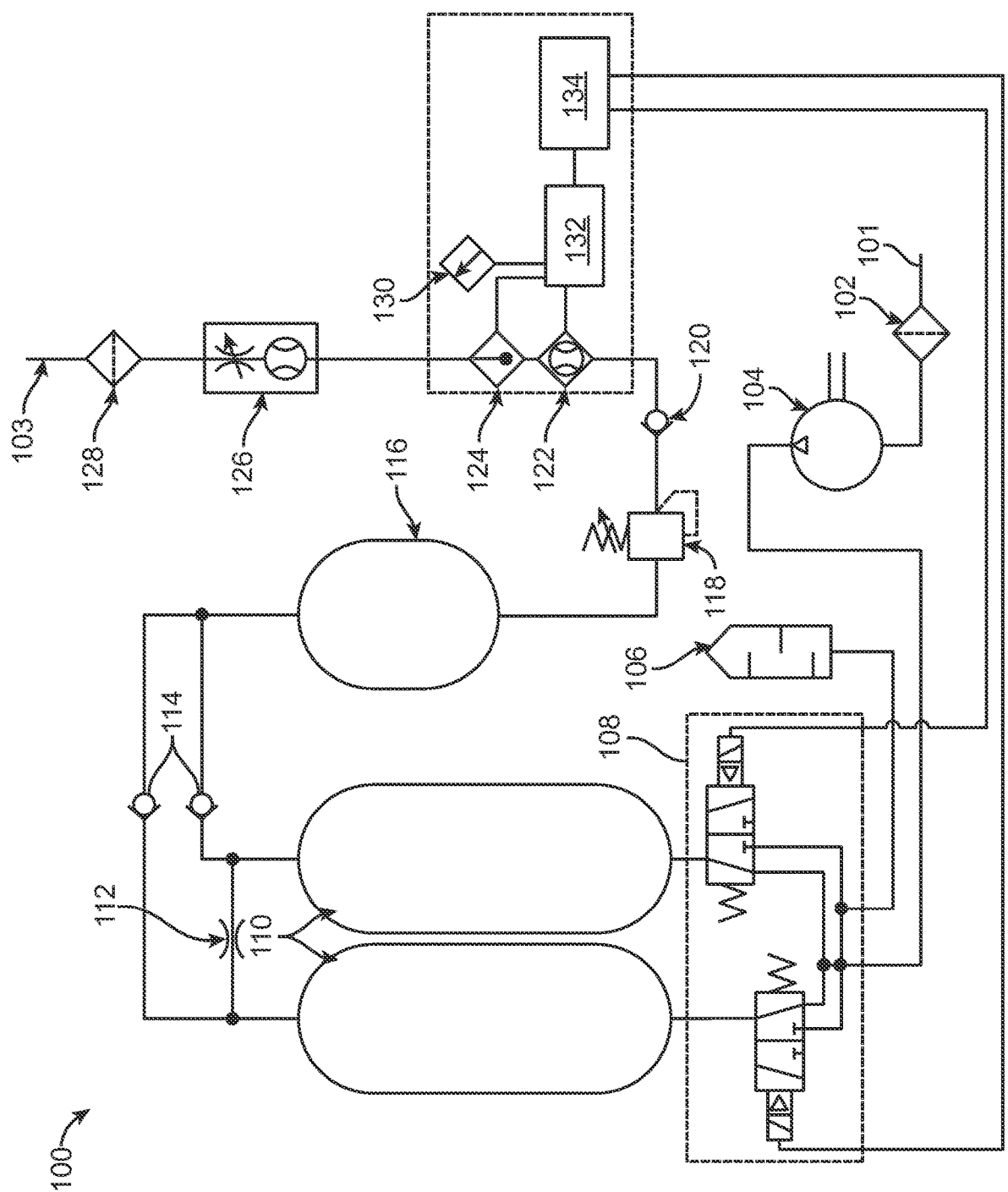
FIG. 1 illustrates an oxygen concentrator executing a control circuit to control the flow of oxygen produced by the oxygen concentrator.

FIG. 1 illustrates a schematic diagram of a gas concentrator system in which a compressor applies pressurized gas to two or more separating elements such as sieve beds to adsorb at least one gas species from the pressurized gas to provide an enriched gas product. For purposes of description, the system is described in an example context of being an oxygen concentrator system that passes a pressurized gas mixture for oxygen supply through a pair of sieve beds that block the flow of nitrogen. It should be appreciated that this is an example and that the system is not limited for use as an oxygen concentrator.

With reference to FIG. 1, the system 100 includes a gas inlet 101 through which a gas, such as ambient air, can flow into the system 100. The system further includes an outlet 103 through which a gas product can be delivered such as to a patient. The system includes one or more fluid lines with lumens through which gas can flow from the inlet toward the outlet. A pair of sieve beds 110 (or other gas separation elements) are positioned along the flow pathway between the gas inlet 101 and the gas outlet 103. It should be appreciated that more than two sieve beds can be used in the system. Fluid control valves 108 regulate the flow of gas to the sieve beds 110, as described in more detail below. The control valves 108 can be any of a variety of types including, for example, solenoid valves or rotary valves.

The valves 108 are communicatively coupled to a valve controller 134 which is coupled to a microprocessor 132. In addition, the system 100 includes an ambient temperature sensor 124 and an ambient pressure sensor 130 that are coupled to the system 100 and/or the valve controller 134. The system further includes a flow rate sensor 122 that measures flow rate of gas toward the gas outlet 103. As described in further detail below, the controller 134 selectively controls periods of pressurizing, equalizing, and venting of the sieve beds based at least on at least two of the measured flow rate, a measured ambient temperature and the measured ambient pressure. The controller can control the time periods of pressurizing, equalizing, and/or venting of the sieve beds independent of one another within a cycle in addition to the overall cycle time for any combination of pressurizing, equalizing, and venting.

The system 100 can also include other components that assist in the functioning of gas concentration. For example, an air compressor 104 is positioned in the flow line between the air inlet 101 and the sieve beds 110. The air compressor 104 compresses or pressurizes air from the inlet prior to its entry into the sieve beds 110. A filter 102 can also be positioned in the flow line for filtering of the gas. The system 100 also includes a purge or vent outlet 106 through which nitrogen rich gas can be vented from the system, as described more fully below.

With reference still to FIG. 1, the sieve beds 110 may have outlet ports that are connected together through a calibrated crossover orifice 112 that permits a controlled flow of oxygen enriched gas to flow from the highest pressure sieve bed to the lowest pressure sieve bed such as to equalize pressure between the sieve beds. A pair of check valves 114 regulate fluid flow out of the sieve beds toward an oxygen product tank 116. A pressure regulator 118 may be positioned in the flow line between the oxygen product tank 116 and the gas outlet 103. The pressure regulator 118 steps the oxygen rich product gas pressure down to reduce high pressure risk to the patient.

Other components can be positioned in or coupled to the flow line including, for example, a check valve 120, one or more filters 128, and a flow meter 126. The check valve 120 isolates the sieve beds 110 when the unit is turned off by eliminating gas back flow. It should be appreciated that other components can be included in the system 100 and that the system 100 is not limited to the specific configuration shown in FIG. 1.

The operation of the system 100 is now described. Ambient air flows into the air compressor 104 through the air inlet 101. The air compressor 104 provides filtered, compressed (pressurized) air toward the two or more valves 108, which control the flow of the compressed air to the sieve beds. Each sieve bed is partially filled with a suitable filter material that allows passage of one type of gas while blocking passage of another type of gas. In this non-limiting example, the sieve beds 110 allow passage of oxygen while retaining nitrogen. Gases other than nitrogen, such as argon, can also be adsorbed.

The valves 108 are coupled to and/or controlled by the valve controller 134 and the microprocessor 132 using sensor inputs from at least two of the flow sensor 122, the ambient temperature sensor 124, and the ambient pressure sensor 130. Air is directed cyclically through each sieve bed 110 pursuant to a pressurizing/separation mode, a pressure equalizing mode, and a venting/purging mode. According to one aspect of operation, the controller selectively controls at least one of the periods of pressurizing, equalizing, and venting of the sieve beds based on the measured flow rate, ambient temperature, and ambient pressure in order to reduce peak pressures and compressor loading. That is, the controller can independently control the time period or any aspect of each period of pressurizing, equalizing, and venting and can also control the time period of an entire cycle. The controller can control based on at least two of a measured flow rate, ambient temperature, and ambient pressure.

The controller 134 controls the valves 108 to connect an inlet side of each sieve bed to the air compressor 104 for separating gas through that sieve bed or to the purge outlet 106 for selectively venting the sieve bed to atmosphere. The valves can be independently controlled by the controller such that any of the valves can operate independent of any of the other valves. In one mode of operation the valves operate to feed the inlet side of the first sieve bed and purge the second sieve bed by venting its inlet side. In a pressure equalization mode, the valves block the inlet sides of each seabed for pressure equalization through the crossover orifice 112. In the next mode, the valves feed the inlet side of the first sieve bed and purge the second sieve bed by venting its inlet side, and then the valves proceed to another cycle wherein they block the inlet sides of both beds for pressure equalization.

Pursuant to the separation mode the sieve beds alternately operate to separate nitrogen from air in order to produce an oxygen enriched gas product. Each sieve beds functions as a sieve by permitting a flow of oxygen therethrough and blocking the flow of nitrogen. Before the operating sieve bed becomes saturated with nitrogen, the controller 134 operates the valves 108 to connect a different sieve bed to the compressor 104 for producing a flow of oxygen enriched gas and the saturated sieve bed is switched to a purge mode. In the purge mode, the inlet of the saturated sieve bed is vented to atmosphere through the vent outlet 106. The outlets of the sieve beds are connected together via the crossover orifice 112, which permits a limited flow of pressurized oxygen rich product gas to flow to the saturated sieve bed in the purge mode to flush nitrogen from the saturated sieve bed. After nitrogen is purged from the sieve bed, the vented inlet side may be closed to allow the pressure to equalize between the sieve beds in a pressure equalizing mode before the purged sieve bed is switched to the separation mode.

The oxygen rich air from the sieve beds flows into and is collected in the oxygen product tank 116. The oxygen product tank 116 delivers enriched oxygen gas to the patient through the pressure regulator 118, variable area flow meter 126, and the filter 128. Using the flow sensor 122, temperature sensor 124, and the ambient pressure sensor 130, the microprocessor 132 can derive timing values to activate and de-activate the valve controller 134 using predetermined formulas.

The oxygen concentrators described herein can include pressure-swing adsorption (PSA) and/or vacuum-PSA (VPSA) gas concentrators; wherein the VPSA cycles also include a pump for the venting step to lower bed pressures below ambient levels for greater capacity in the sieve beds.

Figure 2:
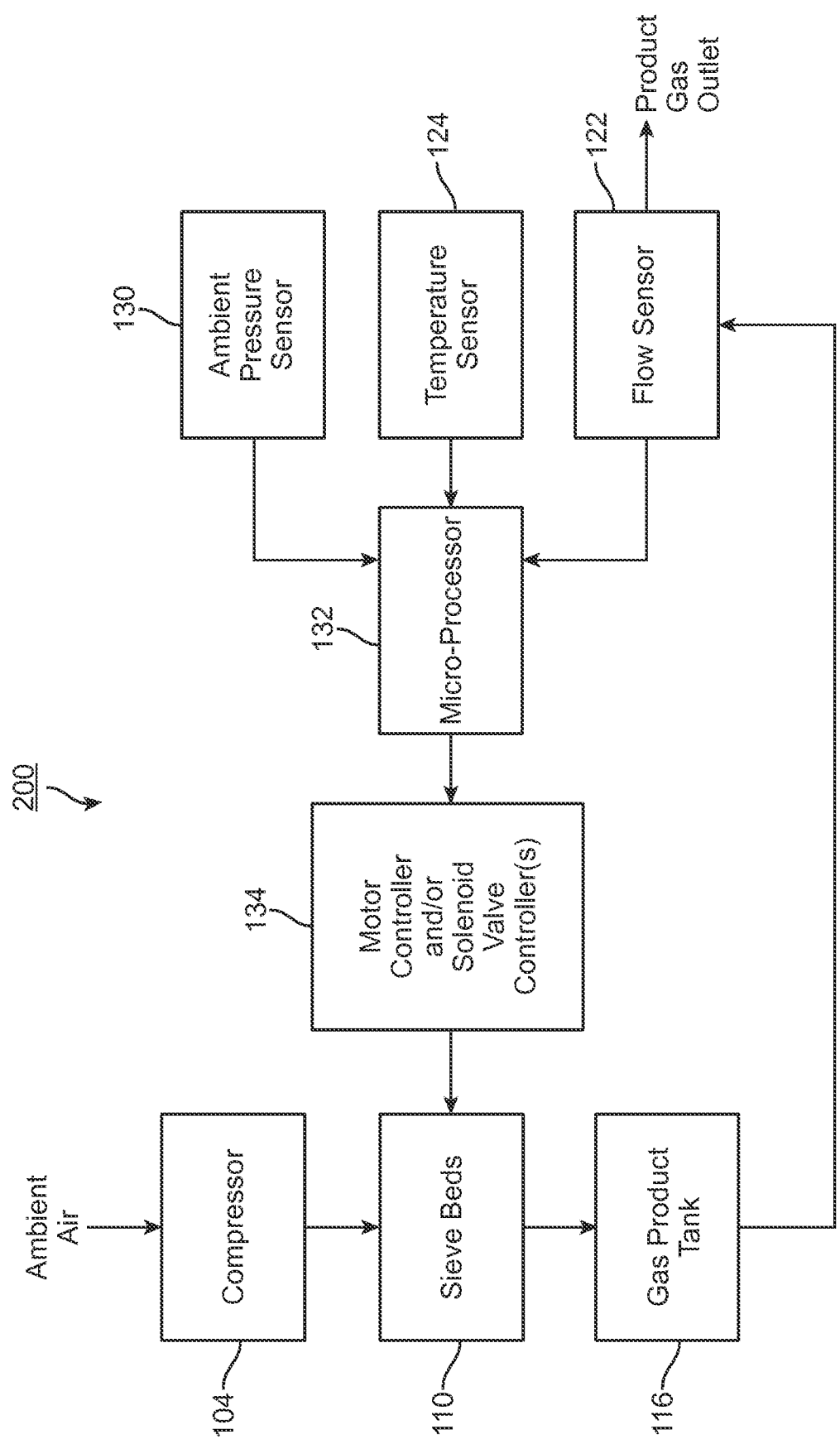
FIG. 2 illustrates a control circuit of the oxygen concentrator.

FIG. 2 illustrates a control circuit 200 of the oxygen concentrator and shows a high level, schematic representation of the system 100. The control circuit 200 includes a compressor 104, molecular sieve beds 110, a gas product tank 116, a controller 134, a microprocessor 132, a flow sensor 122, a temperature sensor 124, and an ambient pressure sensor 130. In one example, the microprocessor 132 and the flow sensor 122 can be implemented on a single circuit board. In another example, the temperature sensor 124 and the ambient pressure sensor 130 can also be implemented on this same circuit board. The controller 134 can be, for example, a motor or a solenoid valve 108 that is controlled by the microprocessor 132.

The flow rate sensor 122 measures the flow rate of oxygen enriched gas when provided to the patient from the gas product tank 116. The temperature sensor 124 measures the ambient temperature. The ambient pressure sensor 130 measures the ambient pressure. The microprocessor 132 receives values of the flow rate of oxygen enriched gas being delivered to patient, ambient temperature, and ambient pressure. The microprocessor 132 then executes a calculation based on the received values of flow rate, ambient temperature, and ambient pressure to control timings of the activation and deactivation of the valves 108 by the controller 134. In an embodiment, the microprocessor includes a software module that permits the manner in which the controller controls the valves and/or the periods of operation of the sieves to be varied. In this manner, the in which the controller operates can be varied by using a software solution without having to mechanically operate the valves.

By controlling the oxygen purification based on oxygen delivery to a patient in accordance with the below referenced mathematical equations (which are non-limiting examples), increases in pressures in the compressor at low oxygen flow rates and reductions in purity of oxygen purified at sieve beds at high oxygen flows can be reduced. In one example, the amount of time a solenoid valve 108 is opened by a controller 134 (supplying compressed air to a sieve bed) can be based on inputs as described above and functionally shown below:

$$V_{open\ time} = (T_{ambient})(P_{ambient})(Ax^2 + Bx + C)$$

Wherein:
$V_{open\ time}$=time valves remain open, sec.
$T_{ambient}$=ambient temperature, ° C.
$P_{ambient}$=ambient pressure, psia
x=current flow rate, lpm
A, B, and C=experimentally determined constants In some alternate implementations, the temperature sensor 124 and the ambient pressure sensor 130 can be optional, and can be included based on a location of the control circuit 200. For example, the temperature sensor 124 and the ambient pressure sensor 130 can be included in the control circuit only at high altitudes (that is, when the control circuit 200 is executed at an altitude more than a threshold value). In such an embodiment, the controller optimizes the periods of operation of the sieve beds based on altitude.

Figure 3:
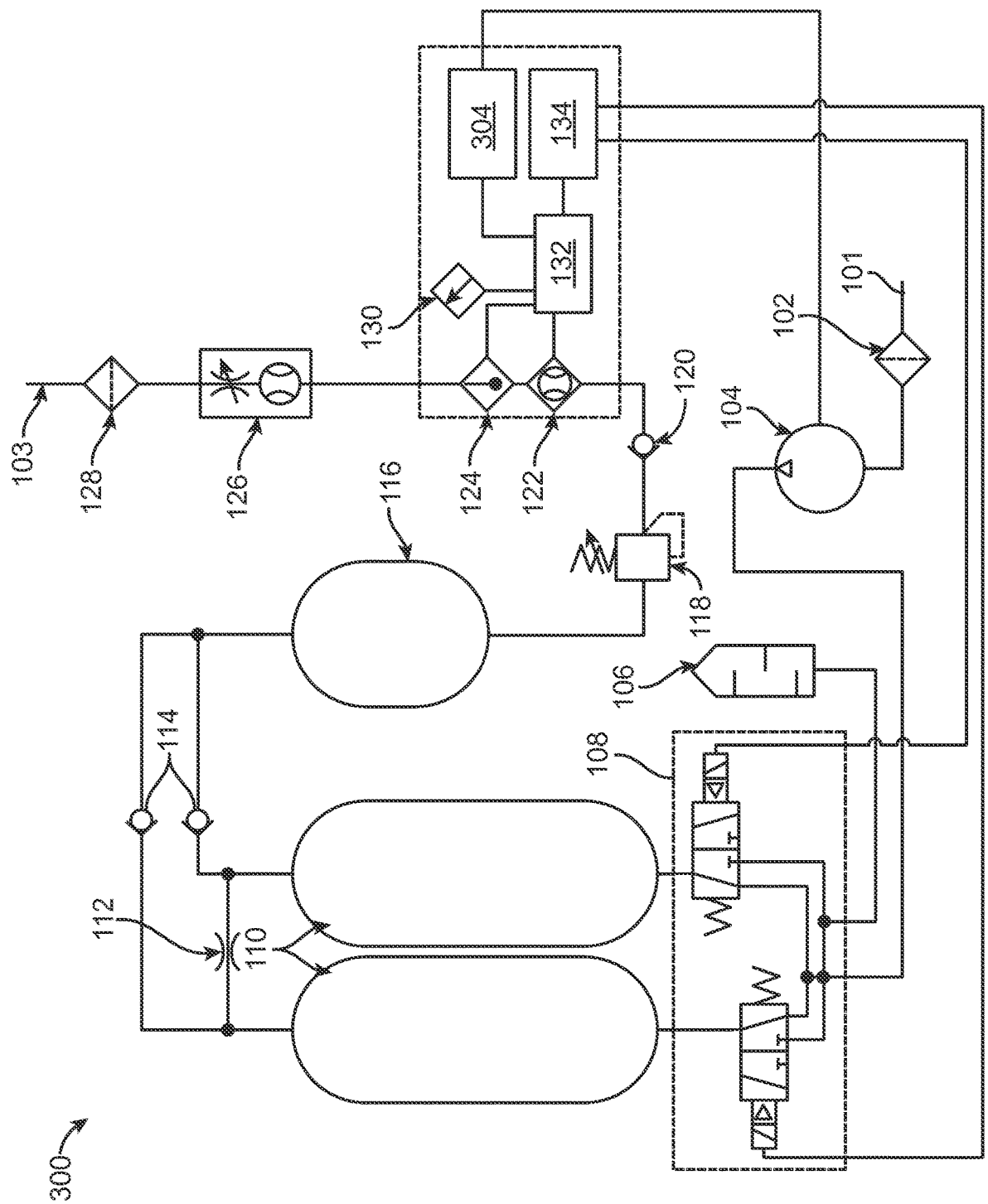
FIG. 3 illustrates an alternative implementation of the control circuit of the oxygen concentrator.

FIG. 3 illustrates one example of an alternative implementation of the control circuit 200 of the oxygen concentrator 100. The control circuit of oxygen concentrator 300 functions similar to the control circuit 200 with the addition of controlling the output of the air compressor 104 using a motor speed controller 304. The microprocessor 132 can determine, based on inputs from the flow sensor 122, temperature sensor 124, and the ambient pressure sensor 130, the optimal speed at which the air compressor 104 needs to operate for best performance. In addition, the added control approached described above can be used congruently with the control circuit 200.

Various implementations of the subject matter described herein can be realized/implemented in digital electronic circuitry, integrated circuitry, specially designed application specific integrated circuits (ASICs), computer hardware, firmware, software, and/or combinations thereof. These various implementations can be implemented in one or more computer programs. Some implementations can be executed using micro-electro mechanical systems (MEMS). These computer programs can be executable and/or interpreted on a programmable system. The programmable system can include at least one programmable processor, which can have a special purpose or a general purpose. The at least one programmable processor can be coupled to a storage system, at least one input device, and at least one output device. The at least one programmable processor can receive data and instructions from, and can transmit data and instructions to, the storage system, the at least one input device, and the at least one output device.

These computer programs (also known as programs, software, software applications or code) can include machine instructions for a programmable processor, and can be implemented in a high-level procedural and/or object-oriented programming language, and/or in assembly/machine language. As can be used herein, the term "machine-readable medium" can refer to any computer program product, apparatus and/or device (for example, magnetic discs, optical disks, memory, programmable logic devices (PLDs)) used to provide machine instructions and/or data to a programmable processor, including a machine-readable medium that can receive machine instructions as a machine-readable signal. The term "machine-readable signal" can refer to any signal used to provide machine instructions and/or data to a programmable processor.

Although a few variations have been described in detail above, other modifications can be possible. For example, the logic flows depicted in the accompanying figures and described herein do not require the particular order shown, or sequential order, to achieve desirable results. Other embodiments may be within the scope of the following claims.

What is claimed is:

1. A gas concentrator system, comprising:
   a gas compressor that receives and compresses ambient air to provide a supply of pressurized gas mixture;
   at least two gas separation sieve beds configured to adsorb at least one gas species from the pressurized gas mixture from the compressor so as to provide an enriched gas product, wherein the gas separation sieve beds cycle between periods of pressurizing and venting;
   first and second valves that independently regulate flow of the pressurized gas mixture to the sieve beds;
   a fluid line coupled to the gas separation sieve beds, the fluid line providing the enriched gas product toward an outlet;
   a flow rate sensor that measures a flow rate of the enriched gas product as the enriched gas product flows through the fluid line;
   additional sensors coupled to the fluid line, wherein the additional sensors includes at least;
   (a) a temperature sensor coupled to the fluid line, wherein the temperature sensor measures ambient temperature; and
   (b) a pressure sensor coupled to the fluid line, wherein the pressure sensor measures ambient pressure;
   a controller that selectively open the first and second valves for a determined time period in order to control either of the periods of pressurizing and venting of the sieve beds wherein the determined time period is calculated using at least the values obtained from the temperature sensor and the pressure sensor and a derived value based on the measured flow rate of the enriched gas product as the enriched gas product flows through the fluid, where the derived value is a univariate quadratic polynomial and where the measured flow rate is the variable.

2. A gas concentrator system as in claim 1, wherein the enriched gas product is oxygen.

3. A gas concentrator system as in claim 2, wherein the oxygen is directed to a patient for inhalation.

4. A gas concentrator system as in claim 1, wherein the enriched gas product is nitrogen.

5. A gas concentrator system as in claim 4, wherein the nitrogen is directed to a beverage delivery system.

6. A gas concentrator system as in claim 1, wherein the enriched gas product is predominately methane.

7. A gas concentrator system as in claim 6, wherein the methane is directed to a condenser.

8. A gas concentrator system as in claim 1, wherein the gas separation sieve beds cycle between a period of equalizing in addition to the periods of pressurizing and venting.

9. A gas concentrator system as in claim 8, wherein the controller selectively controls the first and second valves to control any of the periods of pressurizing, equalizing and venting of the sieve beds based on at least two of the measured flow rate, ambient temperature, and ambient pressure, thereby reducing peak pressures and compressor loading.

10. A gas concentrator system as in claim 1 further comprising a motor speed controller operatively connected to the controller and the gas compressor and wherein the controller is configured to control an output of the compressor via the motor speed controller based on the measured flow rate, the ambient temperature and the ambient pressure.

11. A gas concentrator system as in claim 10 wherein the controller is configured to determine, based on the measured flow rate, the ambient and the ambient pressure, an optimal operation speed of the compressor.

12. A gas concentrator system as in claim 1 wherein the system is configured to prevent reduction in an oxygen purity level in an enriched gas product to a user.

13. A gas concentrator system as in claim 8 wherein the controller selectively controls the first and second valves to control the periods of pressurizing, equalizing, and venting of the sieve beds based on the measured flow rate, ambient temperature, and ambient pressure, thereby reducing increases in pressures in the compressor at low enriched gas product flow rates to a user and reductions in purity of enriched gas at high enriched gas product flow rates to a user.

14. A gas concentrator system as in claim 1, wherein the controller derives the determined time period such that the determined time period increases with decreasing ambient pressure for a given flow according to:

$$\text{Time period} = (T_{ambient})(P_{ambient})(Ax^2 + Bx + C)$$

wherein:
Time period=time, in seconds, that the valves remain open, T ambient=ambient temperature, P ambient=ambient pressure, x=current flow rate, and wherein A, B, and C, are each constant values of the univariate quadratic function.

15. A gas concentrator system as in claim 1, wherein the controller optimizes either of the periods based on an operating altitude.

16. A gas concentrator system as in claim 1, wherein the controller optimizes any of the periods based on minimizing power consumption.

17. A gas concentrator system as in claim 1, further comprising a software module that can be used to control the manner in which the controller selectively controls the first and second valves to control either of the periods of pressurizing and venting of the sieve beds.

18. A gas concentrator system as in claim 1, wherein the first and second valves are solenoid valves.

19. A gas concentrator system as in claim 1, wherein the first and second valves are rotary valves.

20. A gas concentrator system as in claim 1, wherein the controller optimizes a time amount for any of the periods so as to reduce peak pressures and compressor loading relative to a maximum under full flow of pressurized gas mixture through the fluid line.

21. A gas concentrator system as in claim 1 wherein the controller selectively controls the first and second valves to control the periods of pressurizing and venting of the sieve beds based on the measured flow rate, the ambient temperature and the ambient pressure.

22. A gas concentrator system as in claim 1 further comprising a motor speed controller operatively connected to the controller and the gas compressor and wherein the controller is configured to control an output of the compressor via the motor speed controller based on at least two of the measured flow rate, the ambient temperature and the ambient pressure.

* * * * *